United States Patent [19]

Preobrazhenskaya et al.

[11] 4,261,905
[45] Apr. 14, 1981

[54] METHOD FOR PREPARING FURFURYL ALCOHOL

[76] Inventors: Elizaveta A. Preobrazhenskaya, ulitsa Zelenodolskaya, 27, korpus 6, kv. 51, Moscow; Juldash Mamatov, ulitsa Pushkina, 50, kv. 60, Fergana; Ivan P. Polyakov, ulitsa Kashkarskaya, 200, Fergana; Lidia G. Grankina, ulitsa Kirova, 3, kv. 13, Fergana; Jormukhamat G. Abduganiev, ulitsa Kuvasaiskaya, 201, kv. 14, Fergana; Ildgam A. Bekbulatov, ulitsa Kashkarskaya, 215, Fergana; Alexei M. Degovtsov, ulitsa 16-aya, 139, kv. 64, Rostov-na-Donu; Larisa J. Chivanova, ulitsa Kaspiiskaya, 28, korpus 1, kv. 12, Moscow; Lazar D. Pertsov, ulitsa Zelenodolskaya, 12, kv. 119, Moscow; Bassheva B. Berezina, Malaya Gruzinskaya ulitsa, 38, kv. 27, Moscow, all of U.S.S.R.

[21] Appl. No.: 89,299

[22] Filed: Oct. 30, 1979

[30] Foreign Application Priority Data

Nov. 27, 1978 [SU]  U.S.S.R. .................. 2687764

[51] Int. Cl.$^3$ .......................... C07D 307/44
[52] U.S. Cl. .................................. 260/347.8
[58] Field of Search ..................... 260/347.8

[56] References Cited

U.S. PATENT DOCUMENTS 2,094,975  10/1937  Adkins et al. .............. 260/347.8

FOREIGN PATENT DOCUMENTS 835148  3/1952  Fed. Rep. of Germany .
881514  6/1953  Fed. Rep. of Germany .
2275471  1/1976  France .
147519  8/1960  Hungary .
67674  6/1973  Poland .
77554  10/1977  Poland .

OTHER PUBLICATIONS

Haidegger et al., Chem. Abs., vol. 58, (1962) 90276.

Primary Examiner—Richard Raymond
Attorney, Agent, or Firm—Lackenbach, Lilling & Siegel

[57] ABSTRACT

The method for preparing furfuryl alcohol comprises hydrogenation of furfural in the presence of a mixture of a copper-chromite catalyst promoted with oxides of alkali-earth metals, and ceramic material. This mixture is disposed in four beds at a ratio between the catalyst and the ceramic material of 1:2 in the first bed, 1:1 in the second bed, 2:1 in the third bed and 2.5:1 in the fourth bed downstream of the flow of the mixture of furfural and hydrogen. The hydrogenation process is conducted at an elevation of temperature from 50° to 140° C. under a pressure of from 60 to 65 atm, followed by the introduction of monoethanolamine or hydrazine hydrate into the resulting catalyzate.

5 Claims, No Drawings

METHOD FOR PREPARING FURFURYL ALCOHOL

FIELD OF THE INVENTION

The present invention relates to methods for preparing alcohols pertaining to the furan series and, more particularly, to a method for preparing furfuryl alcohol.

Furfuryl alcohol is used per se as a selective solvent and also as a starting material for the production of resins, varnishes, coatings, and binders for injection-molding mixtures and the like.

BACKGROUND OF THE INVENTION

Furfuryl alcohol is generally produced by catalytic hydrogenation of furfural in a vapor or liquid phase using copper catalysts. Thus, British Pat. No. 734,118 teaches hydrogenation in a vapor phase at a temperature of from 80° to 200° C. in the presence of a copper catalyst containing 50 to 20% of anhydrous sodium silicate. FRG Pat. No. 835,148 teaches the use, as the catalyst, of copper supported on an alkali metal silicate or silicic acid, while FRG Pat. No. 881,544 discloses the use of copper-silicate catalysts promoted with oxides of elements pertaining to Group II of the Periodic System. French Pat. No. 2,250,099 discloses the use of an alloyed copper-aluminum catalyst for hydrogenation of furfurol in the presence of a hydrogenation agent, i.e. gases of the synthesis of ammonia, at a temperature ranging from 100° to 150° C.

Also known in the art is a method (cf. Polish Pat. No. 67674) for preparing furfuryl alcohol and sylvan in the presence of a copper-chromite catalyst promoted with oxides of calcium, barium or zinc at a temperature within the range of from 100° to 300° C. under a pressure of 1 atm or more. Polish Pat. No. 77554 teaches hydrogenation of furfurol with the introduction of a polymerization inhibitor, i.e. triethanolamine. Carrying out processes of hydrogenation of furfural in a vapor phase necessitates the use of cumbersome apparatus due to circulation of a large amount of gaseous compounds in the system. Furthermore, great losses of furfuryl alcohol occur due to polymerization thereof at high temperatures along with the formation of a considerable amount of by-products, as well as lowering of the catalyst activity due to resinification thereof with the polymerization products.

Carrying out the process in a liquid phase eliminates evaporation of furfural and related (due to polymerization) losses; also avoided is the necessity of circulating large volumes of hydrogen. The liquid-phase processes may be exemplified by those described in Patents of Czechoslovakia, France, Hungary and USA. Thus, Czechoslovakian Pat. No. 144018 teaches hydrogenation of furfural under a pressure ranging from 10 to 250 atm and at a temperature of from 70° to 210° C. on a catalyst prepared at a uniform atomic distribution of copper on acidic silica neutralized with sodium or potassium. However, catalysts containing copper supported on a carrier are usually less active than copper-chromite ones.

French Pat. No. 2,275,471 teaches hydrogenation of furfural with hydrogen or hydrogen-containing gas at a temperature ranging from 100° to 160° C. on a catalyst including metallic copper, oxides of metals of Group II and/or Group III of the Periodic System, as well as sodium oxide and a neutral agent, i.e. graphite. Furfural is added to the reactor while being diluted with the reaction products.

However, dilution of furfural with the reaction products, namely with furfuryl alcohol, results in a lowered yield of the desired product due to an additional polymerization of furfuryl alcohol.

Known in the art is a process for preparing furfuryl alcohol by hydrogenation of furfural at a temperature within the range of from 170° to 200° C. under a pressure of from 150 to 220 atm using a suspended copper-chromite catalyst promoted with oxides of metals of Group II (cf. Hungarian Pat. No. 147519).

This prior art process has a disadvantage in its use of high pressure and an additional operation of separating of the catalyst from the reaction products. This operation causes additional losses and is economically inefficient.

Also known in the art is a process for producing furfuryl alcohol in a liquid phase in the presence of a copper-chromite catalyst promoted with oxides of Group II metals at a temperature within the range of from 90° to 175° C. under a pressure of from 30 to 200 kgf/cm$^2$ (400 to 3,000 pounds/sq.in) (cf. U.S. Pat. No. 2,094,975). This process features hindered removal of the reaction heat causing a spontaneous elevation of the reaction temperature. This causes the formation of by-products which lower purity of the resulting furfuryl alcohol and reduce the catalyst activity.

BRIEF SUMMARY OF THE INVENTION

It is an object of the present invention to provide a method for preparing furfuryl alcohol which would make it possible to increase the product output and improve purity of the final product.

This object is accomplished by a method for preparing furfuryl alcohol by way of hydrogenation of furfural on a copper-chromite catalyst promoted with oxides of alkali-earth metals upon heating and under an elevated pressure, wherein, in accordance with the present invention use is made of a mixture of a catalyst and ceramic material which is placed in four layers at the ratio between the catalyst and the ceramic material of 1:2 in the first layer; 1:1 in the second layer; 2:1 in the third layer and 2.5:1 in the fourth layer downstream of the movement of the mixture of furfural and hydrogen. The hydrogenation process is conducted at a gradual elevation of temperature from 50° to 140° C. under a pressure of from 60 to 65 atm, followed by introduction of monoethanolamine or hydrazine hydrate into the resulting catalyzate.

The above-specified process conditions make it possible, firstly, to increase the process productivity when it is conducted continuously and, secondly, to lower the formation of by-products due to improved temperature control of the hydrogenation process, i.e. to increase purity and stability of the final furfuryl alcohol and prolong the service life of the catalyst.

DETAILED DESCRIPTION OF THE INVENTION

The process of preparing furfuryl alcohol is conducted in the following manner.

Furfural is preliminarily mixed with circulating hydrogen: the resulting mixture is heated to a temperature of 50° C. and supplied into the hydrogenation column, wherein furfuryl alcohol is produced. As the catalyst activity is lowered, the process temperature is increased to 140° C. The process temperature below 50° C. does not provide for a sufficient rate of reaction, while temperatures above 140° C. cause the formation of by-products and resinification of the catalyst. The reaction mixture is successively passed through four beds of a tabletted copper-chromite catalyst promoted with oxides of Group II metals, i.e. $CuO-Cr_2O_3-CaO$ (BaO, ZrO)-graphite. The catalyst is produced on the basis of nitrates of barium and/or calcium, copper, ammonium bichromate and ammonium hydroxide as taught in U.S. Pat. No. 2,094,875.

The catalyst is used preferably in an amount of from 0.3 to 0.8% by weight as calculated for furfural.

In accordance with the present invention, the catalyst is mixed with ceramic material at a weight ratio as follows: 1:2 in the first bed; 1:1 in the second bed; 2:1 in the third bed and 2.5:1 in the fourth bed downstream of the flow of the mixture of furfural and hydrogen. This enables better control of the process temperature conditions.

In the method according to the present invention use may be made of any inert ceramic material with a particle size close to the catalyst particle size. The process is conducted under a pressure of from 60 to 65 atm. Monoethanolamine or hydrazine hydrate are added to the resulting hydrogenation products after cooling and separation thereof from the circulating hydrogen. The amount of the supplied amine is defined by the amount of furfural and acids in the reaction products. Then the reaction products are subjected to a continuous rectification.

Monoethanolamine or hydrazine hydrate introduced prior to said rectification provide stabilization of furfuryl alcohol by purifying same from furfural and acids.

The process for the preparation of furfuryl alcohol can be effected both periodically and continuously.

For a better understanding of the present invention, some specific Examples are given hereinbelow by way of illustration.

EXAMPLE 1

Into a reactor there are charged Raschig rings with dimensions of 15×15 mm and, afterwards, successively four beds of a copper-chromite catalyst ($CuO-Cr_2O_3$-CaO-graphite) with a particle size of from 8 to 15 mm mixed with ceramic material at the weight ratio between a catalyst and the ceramic material of 1:2, 1:1, 2:1 and 2.5:1 respectively in the direction of movement of the mixture of furfural and hydrogen.

The total amount of the catalyst charged into the reactor is equal to 750–800 kg and that of the ceramic material is equal to —700–720 kg.

Furfural is continuously fed at the rate of 100 kg/hr for mixing with hydrogen, the mixture being heated to a temperature of 50° C. and delivered to the reaction zone. Hydrogenation is effected at a gradual elevation of temperature from 50° to 140° C. under a pressure of from 60 to 65 atm. The resulting catalyzate is supplied to a vessel, whereinto a stabilizing agent, i.e. monoethanolamine is added at the rate of 0.39% by weight of the catalyzate (the content of furfural and acids in the catalyzate is 0.35% by weight), whereafter it is continuously fed to a rectification unit, wherein the mixture is fractionated under vacuum. There are obtained:

(1) a head fraction boiling within the range of from 30° to 75° C./20 mm Hg—0.61 kg/hr (0.6%);
(2) a basic fraction boiling at 76°–78° C./20 mm Hg—99.96 kg/hr (98%);
(3) bottoms—1.32 kg/hr (1.3%);
(4) losses—0.11 kg/hr (0.1%).

The purity grade of the basic fraction is 99.4%.

EXAMPLE 2

Into a reactor there is charged the catalyst mixed with ceramic material similar to that of Example 1 hereinbefore and furfural in an amount of 70 kg. Thereafter, hydrogen is admitted to the reactor to create a pressure therein of from 60 to 65 atm. Hydrogenation is effected while elevating the temperature from 50° to 140° C. under a pressure of from 60 to 65 atm for 60 minutes. The yield of the catalyzate is 69.4 kg or 98.5% of the theoretical value. The content of the residual furfurol and acids is then determined for calculating the required amount of the stabilizing agent. The content of furfural and acids in the catalyzate is equal to 0.35% by weight of the catalyzate.

Into a 50 l reactor provided with a reflux condenser and a receiving vessel there are charged 30 l (33.75 kg) of the resulting catalyzate and 0.13 kg (0.39% by weight of the catalyst) of hydrazine hydrate. After vacuum distillation, furfuryl alcohol is obtained in a yield of 98.2%.

The fractional composition is as follows:
(1) head fraction boiling within the range of from 30° to 75° C./20 mm Hg—0.20 kg (0.6%);
(2) basic fraction—commercial product, boiling at 76°–78° C. 20 mm Hg—33.16 kg (98.2%);
(3) bottoms—0.33 kg (1.0%);
(4) losses—0.06 kg (0.2%).

The purity grade of the basic fraction is 99.6%.

What is claimed is:

1. In a method for preparing furfuryl alcohol by hydrogenating furfural in the presence of a mixture of a copper-chromite catalyst promoted with alkaline earth metal oxides, the improvement which comprises:

mixing inert ceramic material with said catalyst, said mixture of catalyst and ceramic material being positioned in four beds at a weight ratio of said catalyst to ceramic material, in the first bed of 1:2, in the second bed of 1:1, in the third bed of 2:1 and in the fourth bed of 2.5:1 downstream of the flow of the mixture of furfural and hydrogen; the hydrogenation process being conducted at an elevation of temperature from 50° to 140° C. under a pressure of from 60 to 65 atm, followed by the introduction of monoethanolamine or hydrazine hydrate into the resulting catalyzate.

2. The method of claim 1, wherein the inert ceramic material has a particle size approximating the particle size of said catalyst.

3. The method of any of claims 1 or 2, wherein the amount of monoethanolamine or hydrazine hydrate is sufficient to provide stabilization of the furfuryl alcohol.

4. The method of claim 3, wherein the inert ceramic material consists essentially of Raschig rings.

5. The method of any of claims 1, 2, 3 or 4, wherein the catalyzate is fed to a rectification unit and fractionated under vacuum.

* * * * *